United States Patent
MacDonald

(12) 
(10) Patent No.: US 6,652,557 B1
(45) Date of Patent: Nov. 25, 2003

(54) MECHANISM FOR CAPTURING DEBRIS GENERATED DURING VASCULAR PROCEDURES

(76) Inventor: Kenneth A. MacDonald, 735 Randolph St., Canton, MA (US) 02021

(*) Notice: Subject to any disclaimer, the term of this patent is extended or adjusted under 35 U.S.C. 154(b) by 202 days.

(21) Appl. No.: 09/942,318

(22) Filed: Aug. 29, 2001

(51) Int. Cl.$^7$ ............................................. A61M 29/00
(52) U.S. Cl. .................................................. 606/200
(58) Field of Search .............................. 606/200, 110, 606/127, 198, 108, 159, 113, 114; 604/93.01, 105; 623/1.11

(56) References Cited

U.S. PATENT DOCUMENTS

| | | | | |
|---|---|---|---|---|
| 5,769,816 | A | * | 6/1998 | Barbut et al. ............. 604/93.01 |
| 5,911,734 | A | * | 6/1999 | Tsugita et al. .............. 606/200 |
| 6,235,044 | B1 | * | 5/2001 | Root et al. .................. 606/200 |
| 6,245,088 | B1 | * | 6/2001 | Lowery ....................... 606/200 |
| 6,511,503 | B1 | * | 1/2003 | Burkett et al. ............. 623/1.11 |
| 2002/0169474 | A1 | * | 11/2002 | Kusleika et al. ............ 606/200 |
| 2003/0004541 | A1 | * | 1/2003 | Linder et al. ................ 606/200 |

* cited by examiner

Primary Examiner—David O. Reip
Assistant Examiner—D. Jacob Davis
(74) Attorney, Agent, or Firm—Altman & Martin

(57) ABSTRACT

A surgical capsule of the present invention is positioned in an artery or vein by threading a catheter containing the capsule from a proximal incision in the blood vessel to a location within the blood vessel adjacent to a lesion. The catheter comprises an outer holding sheath, an intermediate deployment sheath, and an inner guide wire, all of which are reciprocable with respect to each other. The capsule includes (1) a control sub-assembly that includes a hub and a plurality of outwardly biased leaf springs, and (2) a filter sub-assembly that includes a porous dome that is capable of permitting fluid flow, but retaining particles. Domes of different porosity may be affixed to the leaf springs. The position of the capsule is controlled by the guide wire. The present invention allows the interchangeability of mesh caps of different diameters and mesh sizes. By using the same capsule and the same deployment method, tines or hooks on the shrouds hold the elasticized rim on the mesh. This arrangement enables rapid changes of mesh caps in the operating room, as well as a reduced inventory of catheters, in which the varied mesh caps are interchangeable. Selection of particular mesh caps in special situations enables the desirable production laminar blood flow, which is desirable from the standpoint of treatment.

18 Claims, 3 Drawing Sheets

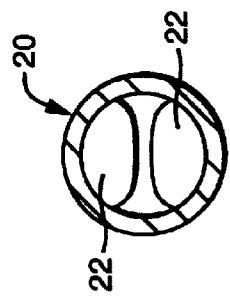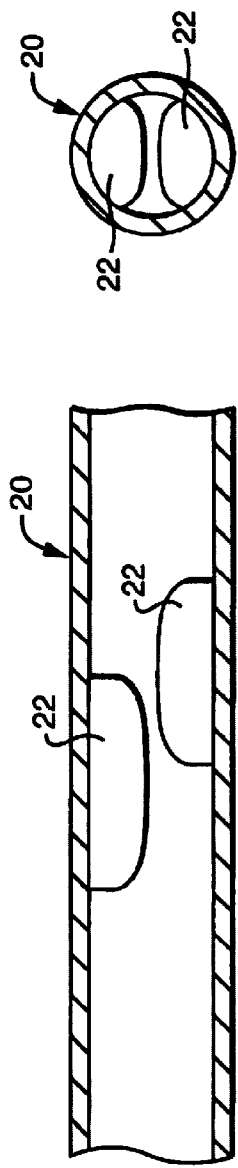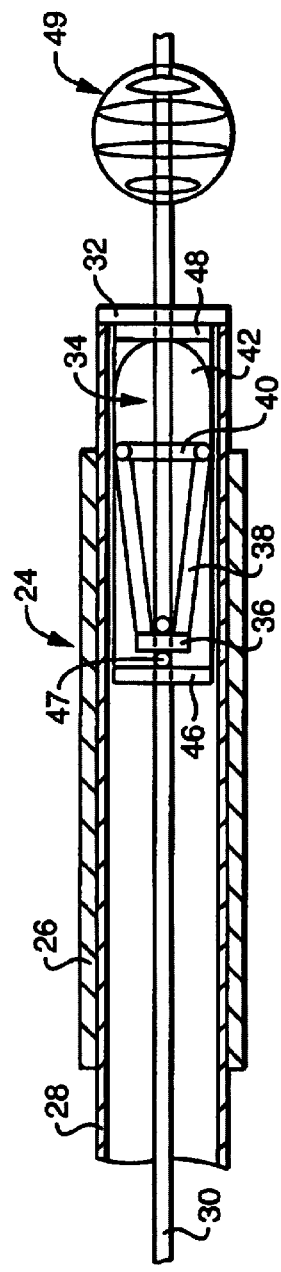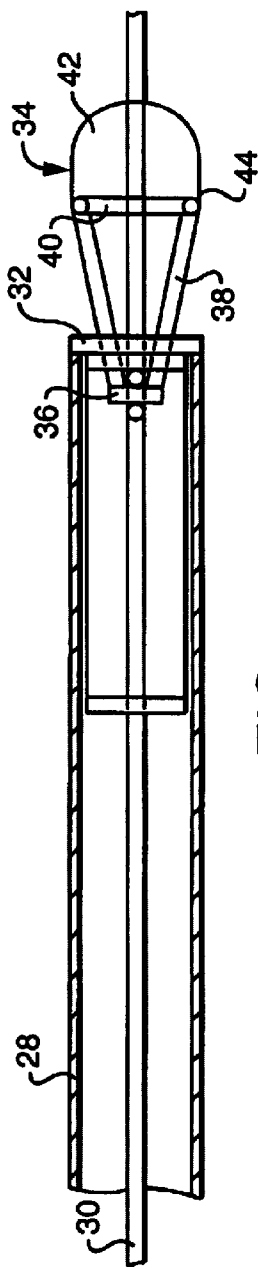

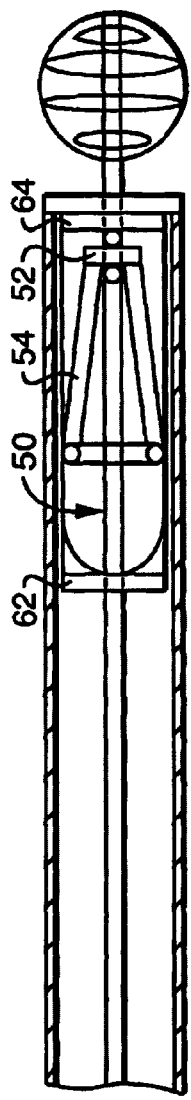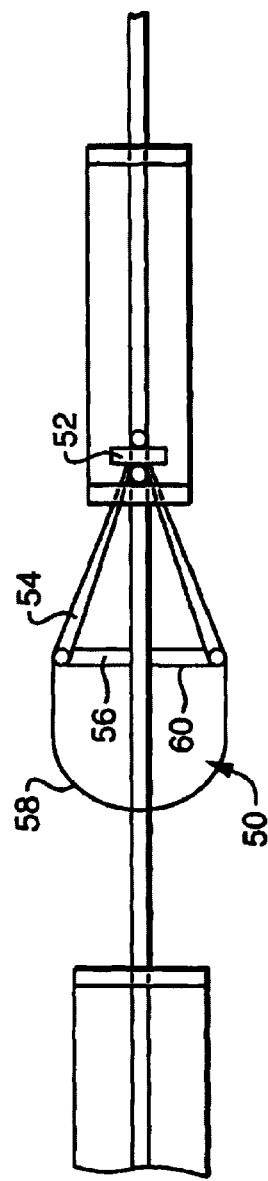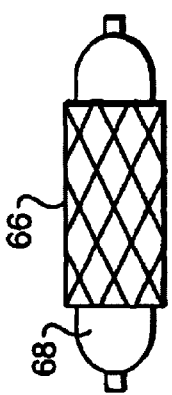

MECHANISM FOR CAPTURING DEBRIS GENERATED DURING VASCULAR PROCEDURES

BACKGROUND OF THE INVENTION

1. Field of the Invention

The present invention relates to the repair of vascular and venous vessels in the body, and, more particularly, to the capture of debris that may result from such repair. As an unwanted result, emboli or clots may flow from the treatment site. Hazards may occur when, as a result of such repair activity, debris flows downstream from the repair to produce stenosis which disrupts flow. Such debris may result in stroke in the case of cerebral vascular treatment or myocardial infarct in the case of coronary vascular treatment. More particularly, the present invention relates to vascular procedures, which involves flattening or fracturing an accumulation of plaque in a blood vessel in order to reduce a blockage that has resulted from the accumulation. Angioplasty, for example, may treat blockages in coronary, leg and carotid arteries.

2. The Prior Art

A number of implantable devices have been used to capture particles dislodged into blood vessels. Because of their size, however, these devices have not been readily adaptable for smaller vessels in major organs. Also, often being surgically implanted, they are difficult to place and remove. In some cases they become a permanent prosthesis. Such devices are disclosed in Mobin-Uddin U.S. Pat. Nos. 3,540,431 and 4,727,873. Kimmel, Jr. U.S. Pat. No. 3,952.747, Simon U.S. Pat. No. 4,425,908, Gianturco U.S. Pat. No. 4,494,531, Molgaard Neilsen U.S. Pat. No. 4,619246, Metals U.S. Pat. No. 4,688,533, Palmaz U.S. Pat. No. 4,793,348, and Palestrant U.S. Pat. No. 4,832,055. A disclosure is made of a filter device in Wholey et al. U.S. Pat. No. 4,723,549, but the device, being part of the catheter, does not allow separate procedures using different catheters to take place without removing the filter device. Similarly other devices, such as Clark U.S. Pat. No. 3,996,938. Roger et al U.S. Pat. No. 5,160,342, and Luther U.S. Pat. No. 4,650,466, disclose devices that are part of the catheter. Bates et.al. U.S. Pat. No. 5,658,296 discloses a catheter that allows a catching mesh that is unattached to a guide wire so that it remains stationary when and if the guide wire is moved. Rasmussen et.al. U.S. Pat. No. 5,133,733 describes a mesh and shroud arrangement that is not removable and replaceable. Daniel et.al. U.S. Pat. No. 5,814,064 describes a catching device on the distal end of the guide wire, which is not contained in a capsule and is not controlled by shrouds. None of these prior art devices can cooperate in effectively controlling a stent.

It is desired to provide a greatly improved debris and emboli protection device that maintains its intended configuration in both high and low pressure fluid environments without interfering with interventional repairs, that has a sufficiently small profile for compatibility with small blood vessels such as the coronary or carotid arteries, and that can easily and safely be removed with the captured debris and emboli following intervention.

SUMMARY OF THE INVENTION

The present invention contemplates a system and process for capturing debris during angioplasty or the like, wherein a catheter is threaded through a proximal incision into an artery or other vessel and thence to a distal location therewithin, at which treatment is to be administered. The catheter comprises an outer holding sheath, an intermediate deployment sheath, and an inner guide wire, all of which are reciprocable with respect to each other. At the distal end of the deployment sheath is a structural ring. At the distal extremity of the guide wire is a surgical capsule, which is retained within the free end of the deployment sheath before use and is extended through the structural ring from the free end of the deployment sheath when in use. The surgical capsule includes a rearward hub that is affixed to the guide wire, a plurality of shrouds in the form of outwardly biased leaf-springs that have rearward extremities affixed to the hub and that extend forwardly from the hub, an elastomeric ring that is affixed to the forward ends of the shrouds, and a mesh cap having a rim that is affixed to the elastomeric ring. The arrangement is such that: when the capsule is un-deployed, i.e. when the capsule is withdrawn into the deployment sheath by the guide wire, the free ends of the shrouds and the rim of the mesh cap are constricted by the inner wall of the deployment sheath; and when the capsule is deployed, i.e. when the capsule is extended from the deployment sheath by the guide wire, the free ends of the shrouds and the rim of the mesh cap are spring pressed by the shrouds into contact with the wall of the blood vessel into which the catheter has been inserted.

For a fuller understanding of the nature and objects of the present invention, reference is made to the following specification, which is to be taken in connection with the accompanying drawings, wherein:

BRIEF DESCRIPTION OF THE DRAWINGS

FIG. 1 is a longitudinal cross-section of a diseased artery that is partly obstructed by plaque;

FIG. 2 is a transverse cross-section of the artery of Fig. 1;

FIG. 3 is a transverse cross-section of part of a catheter showing an un-deployed surgical capsule embodying the present invention;

FIG. 4 is a transverse cross-section of the catheter of FIG. 3 showing the partially deployed surgical capsule of FIG. 3 in accordance with the present invention;

FIG. 8 is a transverse cross-section of part of a catheter showing a reversely oriented un-deployed surgical capsule embodying the present invention;

FIG. 9 is a transverse cross-section of the catheter of FIG. 8 showing the reversely oriented surgical capsule of FIG. 8, fully deployed; and FIG. 10 illustrates a stent for association with a catheter pursuant to the present invention.

DETAILED DESCRIPTION OF THE PREFERRED EMBODIMENTS

FIGS. 1 and 2—a Diseased Artery

FIG. 1 depicts a diseased artery 20 that is partly obstructed by plaque 22. FIG. 2 is a cross section of this artery. During the repair of such an artery, hazards can occur when loosened debris flows downstream from the repair site. This, in turn, can plug off other smaller vessels in the system.

Different methods, such as balloon angioplasty, involve fracturing the plaque, which can result in the production of distal emboli and clots. This debris can result in occlusion of distal vessels. Occlusion of the distal vessels can result in stroke in the case of cerebral vascular treatment or myocardial infarct in the case of coronary vascular treatments. The outcome can be a potentially major medical complication. It is thus advantageous to place a capture device downstream of the proposed repair prior to the initiation of repair activity. This capture device may include a mesh which is intended to permit a continuation of the flow of blood, but to prevent escape of debris. The purpose of the present invention is to capture and extract debris with minimal disruption of blood flow in an artery or vein.

Figure 5:
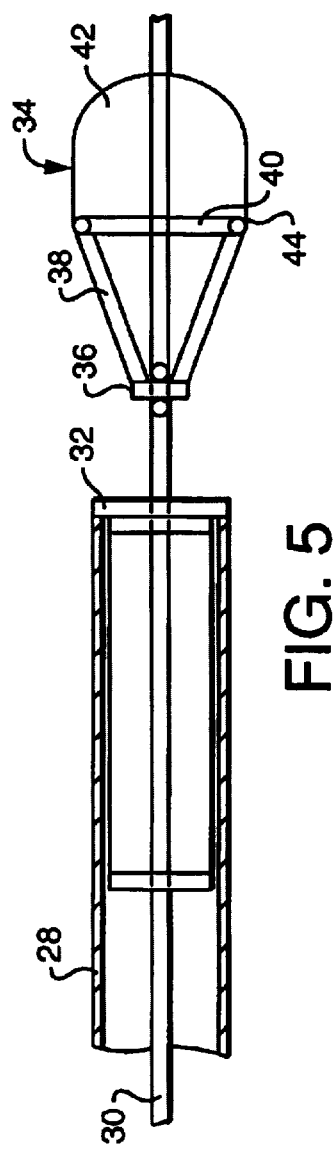
FIG. 5 is a transverse cross-section of the catheter of FIG. 3 showing the fully deployed surgical capsule of Fig. 3 in accordance with the present invention.

FIGS. 3, 4 and 5—Catheter with Forwardly Directed Capsule

As shown in FIGS. 3, a catheter 24 embodying the present invention comprises an outer holding sheath 26, an intermediate deployment sheath 28. and an inner guide wire 30, all of which are reciprocable with respect to each other. For clarity, outer holding sheath 26 is omitted from FIGS. 4 and 5. At or near the distal end of the deployment sheath and affixed thereto is a structural ring 32. Close to the distal extremity of guide wire 30 is a surgical capsule 34, which is retained within the free end of deployment sheath 28 before use and is extended through structural ring 32 from the free end of the deployment sheath when in use. Surgical capsule 34 includes: a rearward hub 36 that is affixed to guide wire 30, a plurality of shrouds 38 in the form of outwardly biased leaf-springs that have rearward extremities affixed to hub 36 and that extend forwardly from the hub; an elastomeric ring 40 that is affixed to the forward ends of shrouds 38; and a mesh cap 42 in the shape of a forwardly directed dome having a rearward rim 44 that is affixed to the elastomeric ring. Capsule 34 is positioned between forward and rearward guides that are in the form of rings 46 and 48, which establish a cage that is moveable within deployment sheath 28. In the present embodiment, these rings are composed of a polymer such as that sold by duPont under the trade designation Teflon for the purpose of easing reciprocal movement of capsule 34 within deployment sheath 28. A pair of stops extending from and anchored to guide wire 30 control movement of capsule 34 within the cage established by rings 46 and 48, and the position of the cage within deployment sheath 28.

The arrangement is such that: when capsule 34 is un-deployed, i.e. when capsule 34 is withdrawn into deployment sheath 28 by guide wire 30, the free ends of shrouds 38 and the rim mesh cap 42 are constricted by the inner wall of the deployment sheath; and when capsule 34 is deployed, i.e. when capsule 34 is extended from deployment sheath 28 by guide wire 30, first as shown in FIG. 4 and then as shown in FIG. 5, the forward ends of shrouds 38 and the rim 44 of mesh cap 42 are spring pressed by the shrouds into contact with the wall of the blood vessel into which the catheter has been inserted.

Figure 6:
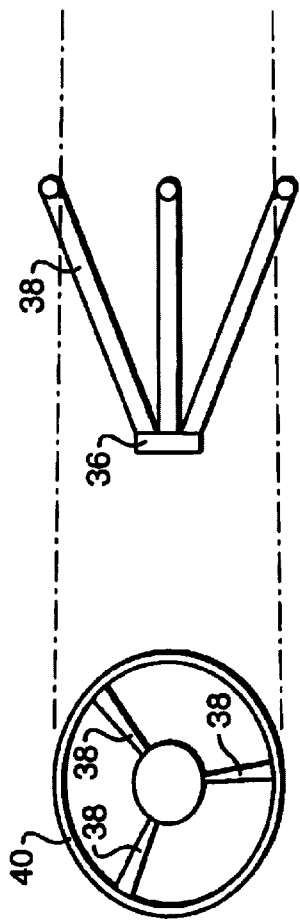
FIG. 6 is a diagram illustrating the relationships between two components of the surgical capsule of FIG. 4.
Figure 7:
FIG. 7 is a diagram illustrating the relationships between two further components of the surgical capsule of FIG. 4.

FIGS. 6 and 7—The Exchangeable Mesh Cap

The mesh cap is a shaped form that fits snugly into an artery or vein. Its domed shape and flexible circumference are determined by the outwardly biased shrouds and the elastomeric rim the shrouds control. The mesh cap and the shrouds are detachably held together by hooks, one of which is shown at 43 in FIG. 7, on the shrouds that join the elastomeric rim at intervals. Preferably, the mesh is composed of an inert material, such as a polyethylene or a polycarbonate, that is perforated with pores of a selected diameter and a selected distribution to enable selected blood flow. The capsule is axially aligned using angioplasty. The shrouds, which are three or four in number, preferably three, are composed of stainless steel. The elastomeric rim is enabled to constrict when the shrouds are withdrawn into the deployment sheath, and expands under the bias of the shrouds when the shrouds are projected from the deployment sheath.

FIGS. 8 and 9—Catheter with Rearwardly Directed Capsule

As shown in FIGS. 8 and 9, the catheter comprises an outer holding sheath (not shown for clarity), an intermediate deployment sheath, and an inner guide wire, all of which are analogous to their counterparts in FIGS. 3, 4 and 5. At or near the distal end of the deployment sheath and affixed thereto is a structural ring that is analogous to its counterpart in FIGS. 3, 4 and 5. Close to the distal extremity of the guide wire is a surgical capsule 50 that is analogous to its counterpart in FIGS. 3, 4 and 5, except that its orientation is reversed. As shown capsule 50 includes a forward hub 52 that is affixed to the guide wire, a plurality of shrouds 54 in the form of outwardly biased leaf-springs that have forward extremities affixed to hub 52 and that extend rearwardly from the hub, an elastomeric ring 56 that is affixed to the rearward ends of shrouds 54, and a mesh cap 58 in the shape of a rearwardly directed dome having a forward rim 60 that is affixed to the elastomeric ring. Capsule 50 is positioned between rearward and forward guides that are in the form of guide rings 62 and 64 that are analogous to guide rings 46 and 48 in FIGS. 3,4 and 5.

The arrangement is such that: when the capsule is un-deployed, i.e. when capsule is withdrawn into the deployment sheath by the guide wire, the free ends of shrouds 54 and the rim of mesh cap 50 are constricted by the inner wall of the deployment sheath; and when the capsule is deployed, i.e. when the capsule is extended from the deployment sheath by the guide wire, the free ends of shrouds 54 and the rim 60 of mesh cap 56 are spring pressed by the shrouds into contact with the wall of the blood vessel into which the catheter has been inserted. A primary application of the arrangement of FIGS. 8 and 9 is venous intervention. Here, the fluid flow for catching emboli (i.e. vein versus artery) is in a direction that is the reverse of that in arterial flow. In this application, the capsule, including mesh cap 50, is reversed and adapted to catch hazards that may be flowing in the venous direction. For example, the reversed mesh cap here is capable of catching emboli that have become detached from a thrombosis that is flowing in a direction en route to the heart. In the venous system, the capsule initially is in the placement sheath with the positions of the ferrules on the guide wire reversed.

FIG. 10—Catheter with Stent Deployment Accessory

A capsule that is constructed in the manner of the present invention is adapted to cooperate in the positioning of a stent 66. Stent 66 is a stainless steel, tubular, flexible wire cage, which has an initial diameter that is smaller than the blood vessel, and an expanded diameter by which the stent abuts against the wall of the vessel after it is deployed at a desired site. The blood flow in an artery may be sufficiently rapid and turbulent to make it difficult to properly deploy the stent. The concentration of perforations in the mesh cap may modulate the flow, i.e. the Reynolds number, which indicates the relationship between laminar and turbulent flow. When installing a stent, the mesh cap of the capsule is provided with a relatively small number of perforations, by virtue of which the Reynolds number of the blood flow is reduced and laminar flow results. As shown, stent 66 is deployed at the distal end of the guide wire by a balloon 68 which is carried by the guide wire. After being positioned, the balloon, which is fed with fluid through the deployment sheath, expands the stent and then is deflated and withdrawn.

OPERATION

In operation, a surgical capsule of the present invention is positioned in an artery or vein by threading a catheter containing the capsule from a proximal incision in the blood vessel to a location within the blood vessel adjacent to a lesion. The catheter comprises an outer holding sheath, an intermediate deployment sheath, and an inner guide wire, all of which are reciprocable with respect to each other. There is a structural ring of predetermined constant internal and external diameter at the distal end of the holding sheath. The capsule includes (1) a control sub-assembly that includes a hub and a plurality of outwardly biased leaf springs, and (2) a filter sub-assembly that includes a porous dome that is capable of permitting fluid flow, but retaining particles. Domes of different porosity may be affixed to the leaf springs. The capsule, when affixed to the guide wire, is moved through the deployment sheath within a cage that includes a pair of spaced rings. The position of the cage is controlled by the guide wire. The present invention allows the interchangeability of mesh caps of different diameters and mesh sizes. By using the same capsule and the same deployment method, tines or hooks on the shrouds hold the elasticized rim on the mesh. This arrangement enables rapid changes of mesh caps in the operating room, as well as a reduced inventory of catheters, in which the varied mesh caps are interchangeable. Selection of particular mesh caps in special situations enables the desirable production of laminar blood flow, which is desirable from the standpoint of treatment.

For full deployment in an artery, the relationships of the stops, the rings of the cage, and the structural ring are such that the cage is moved by the guide wire until stopped by the structural ring and the capsule is moved from within the cage and through the structural ring from the free end of the deployment sheath. During these steps, the remote ends of the leaf springs expand to spread the perimeter of the porous dome until it snugly fits against the inner wall of the artery.

For full deployment in a vein, the relationships of the stops, the rings of the cage, and the structural ring are such that the cage is moved by the guide wire through the structural ring and its movement is continued until the capsule is free of the cage. During these steps, the remote ends of the leaf springs expand to spread the perimeter of the porous dome until is snugly fits against the inner wall of the vein.

In procedures involving arteries and veins in the extremities, femoral and staphenous, both the forwardly.directed and the rearwardly directed capsules may be deployed to perform their previously described functions.

Generally, the catheter of the present invention can be used in any blood vessel. In particular since a primary goal of the invention is use in small blood vessels, such as the carotid or coronary arteries, it is essential to minimize the size, i.e. the diameters of the sheaths. This means restricting its size to, diameters and lengths necessary to allow the device to pass freely through the blood vessels. Sizes encountered have the following ranges: guide wire —0.035" maximum with a-clearance of 0.002" to 0.004"; holding sheath —I.D. 0.065" to 0.100", O.D. 0.095" to 0.115"; collapsible mesh—O.D. 0.014" to 0.100"; capsule I.D. approximately 0.037", O.D. approximately 0.047". The Reynold's number, which is a measure of the relationship between laminar and turbulent flow, is governed by such measures as blood velocity, blood pressure, blood viscosity, blood density, and blood vessel diameter. Normally, the desirable value of the Reynold's number in blood flow is <2000. There is a direct relationship between the Reynold's number and the number of perforations in the mesh cap. By controlling the density of perforations in the mesh cap, the Reynold's number can be controlled.

What is claimed is:

1. A surgical system comprising a catheter having an outer holding sheath, an intermediate deployment sheath, an inner guide wire, and a capsule affixed to said guide wire, said holding sheath, said deployment sheath and said guide wire being reciprocable with respect to each other:

(a) a structural ring at the distal end of said holding sheath;

(b) a cage including a pair of spaced rings for holding said capsule while moved within said deployment sheath;

(c) said surgical capsule including a hub that is affixed to said guide wire and a plurality of shrouds in the form of outwardly biased leaf-springs;

(d) said leaf-springs having anchored extremities that are affixed to said hub and free extremities that extend from said hub;

(e) an elastomeric ring that is affixed to said free extremities;

(f) a mesh cap having a rim that is affixed to said elastomeric ring;

(g) when said capsule is un-deployed, said free ends and said rim being constricted by the inner wall of said deployment sheath;

(h) when said capsule is deployed, said free ends and said rim being spring pressed by said leaf springs into contact with a wall of a blood vessel into which said catheter has been inserted.

2. The surgical system of claim 1 wherein said blood vessel is an artery.

3. The surgical system of claim 1 wherein said blood vessel is a vein.

4. The surgical system of claim 1 wherein said hub is affixed to said guide wire by a pair of stops.

5. The surgical system of claim 1 wherein; said guide wire has a diameter of approximately 0.035" with a clearance of 0.002" to 0.004"; said holding sheath has an I.D. in the range of 0.065" to 0.100", and an O.D. in the range of 0.095" to 0.115"; said collapsible mesh has an O.D. in the range of 0.014" to 0.100.

6. The surgical system of claim 1 wherein said rim is detachably connected to said extremities by hooks.

7. A surgical system comprising a catheter having an outer holding sheath, an intermediate deployment sheath, an inner guide wire, and a capsule affixed to said guide wire, said holding sheath, said deployment sheath and said guide wire being reciprocable with respect to each other:

(a) a structural ring at the distal end of said holding sheath;

(b) said surgical capsule being retained within the free end of said deployment sheath before use and being extended through said structural ring from the distal end of said deployment sheath when in use;

(c) said surgical capsule including a rearward hub that is affixed to said guide wire and a plurality of shrouds in the form of outwardly biased leaf-springs;

(d) said leaf-springs having rearward extremities that are affixed to said hub and forward extremities that extend forwardly from said hub;

(e) an elastomeric ring that is affixed to said forward extremities;

(f) a mesh cap having a forwardly protruding dome and a rim that is affixed to said elastomeric ring;

(g) when said capsule is un-deployed, said forward ends and said rim being constricted by the inner wall of said deployment sheath;

(h) when capsule is deployed, said forward ends and said rim being spring pressed by said shrouds into contact with a wall of an artery into which said catheter has been inserted.

8. The surgical system of claim 7 wherein the outside diameter of said holding sheath is less than 0.1 inch.

9. The surgical system of claim 7 wherein said mesh cap has a distribution of apertures that produce a Reynolds number less than 2000.

10. A surgical system comprising a catheter having an outer holding sheath, an intermediate deployment sheath, an inner guide wire, and a capsule affixed to said guide wire, said holding sheath, said deployment sheath and said guide wire being reciprocable with respect to each other:

(a) a structural ring at the distal end of said holding sheath;

(b) said surgical capsule being retained within the free end of said deployment sheath before use and being extended through said structural ring from the distal end of said deployment sheath when in use;

(c) said surgical capsule including a forward hub that is affixed to said guide wire and a plurality of shrouds in the form of outwardly biased leaf-springs;

(d) said leaf-springs having forward extremities that are affixed to said hub and rearward extremities that extend rearwardly from said hub;

(e) an elastomeric ring that is affixed to said rearward extremities of said leaf-springs;

(f) a mesh cap having a rearwardly protruding dome and a rim that is affixed to said elastomeric ring;

(g) when said capsule is un-deployed, said rearward ends of said leaf-springs and said rim being constricted by the inner wall of said deployment sheath;

(h) when capsule is deployed, said rearward ends of said leaf springs and said rim being spring pressed by said leaf-springs-into contact with a wall of a vein into which said catheter has been inserted.

11. The surgical system of claim 10 wherein the outside diameter of said holding sheath is less than 0.1 inch.

12. The surgical system of claim 10 wherein said mesh cap has a distribution of apertures that produce a Reynolds number less than 2000.

13. A surgical procedure comprising:

(a) first inserting a catheter into a blood vessel, said catheter having an outer holding sheath, an intermediate deployment sheath, an inner guide wire, and a capsule affixed to said guide wire, said holding sheath, said deployment sheath and said guide wire being reciprocable with respect to each other;

(b) a structural ring at the distal end of said holding sheath;

(c) a cage including a pair of spaced rings for holding said capsule while moved within said deployment sheath;

(d) said surgical capsule including a hub that is affixed to said guide wire and a plurality of shrouds in the form of outwardly biased leaf-springs;

(e) said leaf-springs having anchored extremities that are affixed to said hub and free extremities-that extend from said hub;

(f) an elastomeric ring that is affixed to said free extremities;

(g) a mesh cap having a rim that is affixed to said elastomeric ring;

(h) said capsule being un-deployed with said free ends and said rim being constricted by the inner wall of said deployment sheath; and (i) next, deploying said capsule so that said free ends and said rim are spring pressed by said leaf springs into contact with a wall of said blood vessel;

(j) next, performing a series of surgical steps within said blood vessel; and (k) then retracting said capsule into said deployment sheath, said deployment sheath into said holding sheath and said catheter from said blood vessel.

14. The surgical procedure of claim 13 wherein said blood vessel is an artery.

15. The surgical procedure of claim 13 wherein said blood vessel is a vein.

16. A surgical procedure comprising:

(a) first inserting a catheter into a vascular channel, said catheter having an outer holding sheath, an intermediate deployment sheath, an inner guide wire, and a capsule affixed to said guide wire, said holding sheath, said deployment sheath and said guide wire being reciprocable with respect to each other;

(b) a structural ring at the distal end of said holding sheath;

(c) a cage including a pair of spaced rings for holding said capsule while moved within said deployment sheath;

(d) said surgical capsule including a hub that is affixed to said guide wire and a plurality of shrouds in the form of outwardly biased leaf-springs;

(e) said leaf-springs having anchored extremities that are affixed to said hub and free extremities that extend from said hub;

(f) an elastomeric ring that is affixed to said free extremities;

(g) a mesh cap having a rim that is affixed to said elastomeric ring;

(h) said capsule being un-deployed with said free ends and said rim being constricted by the inner wall of said deployment sheath; and (i) next, deploying said capsule so that said free ends and said rim are spring pressed by said leaf springs into contact with a wall of said vascular channel;

(j) next, performing a series of surgical steps within said vascular channel; and (k) then retracting said capsule into said deployment sheath, said deployment sheath into said holding sheath, and said catheter from said vascular channel.

17. The surgical procedure of claim 16 wherein said vascular channel is an artery.

18. The surgical procedure of claim 16 wherein said vascular channel is a vein.

* * * * *